(12) United States Patent
Fuleki et al.

(10) Patent No.: US 9,976,916 B2
(45) Date of Patent: May 22, 2018

(54) AIR SENSOR WITH DOWNSTREAM FACING INGRESS TO PREVENT CONDENSATION

(71) Applicant: NATIONAL RESEARCH COUNCIL OF CANADA, Ottawa (CA)

(72) Inventors: Dan Fuleki, Chelsea (CA); Daniel Knezevici, Ottawa (CA)

(73) Assignee: National Research Council of Canada, Ottawa, Ontario (CA)

( * ) Notice: Subject to any disclaimer, the term of this patent is extended or adjusted under 35 U.S.C. 154(b) by 0 days. days.

(21) Appl. No.: 15/303,759

(22) PCT Filed: Apr. 10, 2015

(86) PCT No.: PCT/IB2015/052624

§ 371 (c)(1),
(2) Date: Oct. 13, 2016

(87) PCT Pub. No.: WO2015/159193

PCT Pub. Date: Oct. 22, 2015

(65) Prior Publication Data

US 2017/0045404 A1    Feb. 16, 2017

Related U.S. Application Data

(60) Provisional application No. 61/979,135, filed on Apr. 14, 2014.

(51) Int. Cl.
*G01K 13/02*     (2006.01)
*B64D 15/20*     (2006.01)
(Continued)

(52) U.S. Cl.
CPC ......... *G01K 13/028* (2013.01); *B64D 15/20* (2013.01); *G01K 15/00* (2013.01); *G01M 9/065* (2013.01);
(Continued)

(58) Field of Classification Search
CPC . G01F 1/68; G01F 1/684; G01P 13/02; G01K 13/028

See application file for complete search history.

(56) References Cited

U.S. PATENT DOCUMENTS 3,000,213 A * 9/1961 Eves .................. B64D 15/20
244/134 R
3,425,277 A * 2/1969 Adams ................. G01F 1/684
73/202

(Continued)

FOREIGN PATENT DOCUMENTS

EP      2317293     5/2011
EP      2412952     2/2012

(Continued)

OTHER PUBLICATIONS

Davison, Craig, et al., Naturally Aspirating Isokinetic Total Water Content Probe—Wind Tunnel Test Results and Design Modifications, 2011-38-0036 of SAE International, Jun. 13, 2011.

(Continued)

*Primary Examiner* — Jewel V Dowtin
(74) *Attorney, Agent, or Firm* — Jason E. J. Davis

(57) ABSTRACT

An air flow sensor is provided with an opening facing downstream and having a thin downstream facing edge to prevent condensation or buildup of moisture thereon. The sensor has been found to reduce entrainment of particles in a mixed phase stream. The sensor is suitable for mounting to an aircraft, and to determining air temperature and relative humidity.

20 Claims, 4 Drawing Sheets

(51) Int. Cl.
G01K 15/00 (2006.01)
G01N 1/22 (2006.01)
G01M 9/06 (2006.01)
G01N 27/22 (2006.01)

(52) U.S. Cl.
CPC ......... *G01N 1/2247* (2013.01); *G01N 27/223* (2013.01); *G01K 2013/024* (2013.01)

(56) References Cited

U.S. PATENT DOCUMENTS

| | | | | |
|---|---|---|---|---|
| 3,443,434 | A * | 5/1969 | Baker | G01F 1/6847 73/202.5 |
| 4,131,011 | A * | 12/1978 | Ling | D06F 58/28 73/29.01 |
| 4,468,961 | A * | 9/1984 | Berg | G01P 13/025 116/265 |
| 4,542,650 | A * | 9/1985 | Renken | G01F 1/6965 338/319 |
| 5,191,793 | A * | 3/1993 | Drexel | G01F 1/6847 73/204.22 |
| 6,622,556 | B1 | 9/2003 | May | |
| 6,883,370 | B2 * | 4/2005 | Vincze | G01F 1/6845 73/204.26 |
| 7,124,630 | B2 | 10/2006 | Hanson et al. | |
| 7,370,526 | B1 | 5/2008 | Ice | |
| 7,748,268 | B2 * | 7/2010 | Lull | G01F 1/684 73/204.22 |
| 7,861,585 | B2 * | 1/2011 | Muraoka | G01F 1/6842 73/204.25 |
| 8,104,955 | B2 | 1/2012 | Benning et al. | |
| 8,182,140 | B2 | 5/2012 | Severson | |
| 2005/0241416 | A1 | 11/2005 | DeFriez et al. | |
| 2009/0255323 | A1 | 10/2009 | Butt et al. | |
| 2010/0043573 | A1 | 2/2010 | Carichon et al. | |
| 2011/0314776 | A1 | 12/2011 | Bloom | |
| 2013/0105631 | A1 | 5/2013 | Chen et al. | |

FOREIGN PATENT DOCUMENTS

| | | |
|---|---|---|
| EP | 2510212 | 10/2015 |
| JP | 2004301678 | 10/2004 |

OTHER PUBLICATIONS

Filges, Annette, et al, Initial evaluation of airborne water vapour measurements by the IAGOS-GHG CRDS system, The Smithsonian/NASA Astrophysics Data System ("ADS"), presented at EGU General Assembly 2013, held Apr. 7-12, 2013 in Vienna, Austria, id. EGU2013-9940.

Tang, Qing-Yuan, et al., Fast response resistive humidity sensitivity of polyimide/multi wall carbon nanutubes composite films, Sensors and Actuators B—Chemical (Elsevier Publishing).

Stansbury, Richard, et al., A P-3 Deployable Unmanned Aircraft for Scientific Measurement of Tropical Cyclones, Aerospace Research Central (ARC) Publication—Mar. 29-31, 2011.

Heymsfield, Andrew J., et al., Ice Cloud Particle Size Distributions and Pressure-Dependent Terminal Velocities from In Situ Observations at Temperatures from 0 to -86 C, American Meteorological Society—Journal of the Atmospheric Sciences 2013.

Freeman, Paul, et al., Air data system fault modeling and detection, Control Engineering Practice vol. 21, Issue 10, Oct. 2013, pp. 1290-1301.

Fraczek, Michael, et al., Laser-based air data system for aircraft control using Raman and elastic backscatter for the measurement of temperature, density, pressure, moisture, and particle backscatter coefficient, Optics Info Base—Applied Optics, vol. 51, Issue 2, pp. 148-166 (2012).

Passner, Jeffrey E., et al., Using Real-Time Weather Data from an Unmanned Aircraft System to Support the Advanced Research Version of the Weather Research and Forecast Model, DTIC Online—Information for the Defense Community Report Dates 2010-2012.

Brock, Charles A., et al., Ultrafine particle size distributions measured in aircraft exhaust plumes, Journal of Geophysical Research, vol. 105, No. D21, pp. 26,555-26,567, Nov. 16, 2000.

Hermann, M., et al., Sampling Characteristics of an Aircraft-Borne Aerosol Inlet System, American Meteorological Society, Journal of Atmospheric and Oceanic Technology, vol. 18, Jan. 2001, pp. 7-19.

Price, H.U., et al., Vertical profiles of O3, aerosols, CO and NMHCs in the Northeast Pacific During the TRACE-P and ACE-ASIA experiments, Journal of Geophysical Research, vol. 108, No. D20, 8799, doi:10.1029/2002JD002930, 2003.

International Preliminary Report on Patentability, dated Oct. 18, 2016.

International Search Report and Written Opinion of the International Searching Authority, dated Jul. 27, 2015.

Extended European Search Report dated Oct. 12, 2017.

Price, Heather U. et al. "Vertical profiles of O3, aerosols, CO and NMHCs in the Northeast Pacific during the TRACE-P and ACE-ASIA experiments", Journal of Geophysical Research, vol. 108, No. D20, Jan. 1, 2003.

* cited by examiner

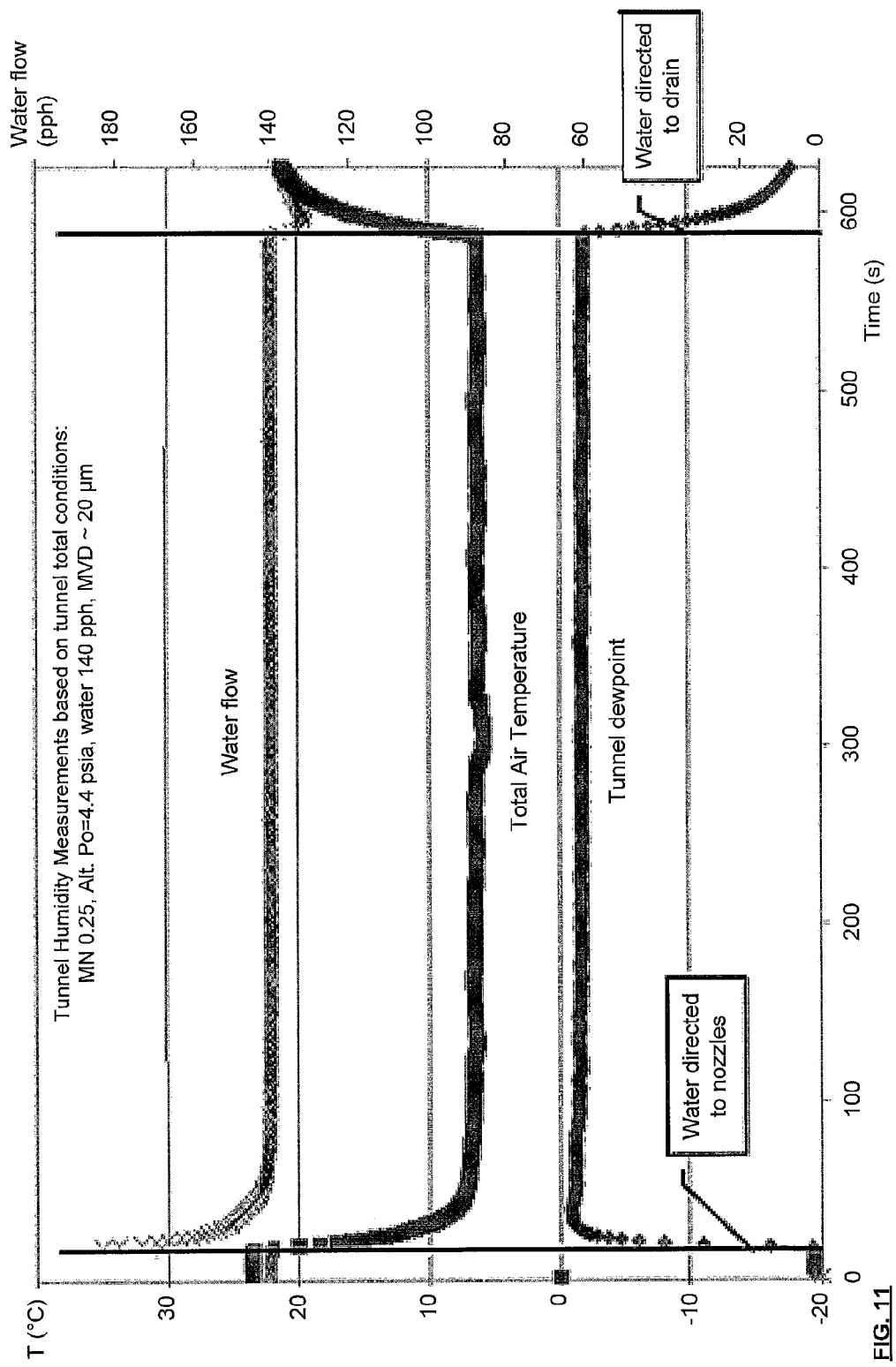

AIR SENSOR WITH DOWNSTREAM FACING INGRESS TO PREVENT CONDENSATION

CROSS-REFERENCE TO RELATED APPLICATIONS

This application is a national phase entry of International Patent Application PCT/IB2015/052624 filed Apr. 10, 2015, which claims the benefit of U.S. Provisional Patent Application Ser. No. 61/979,135 filed Apr. 14, 2014.

FIELD OF THE INVENTION

The present invention relates in general to air sensors, and in particular to temperature, and humidity sensors operable in air flows that may contain ice and/or water droplets.

BACKGROUND OF THE INVENTION

It is desired to measure properties of gas in a flow that may be expected to entrain particles or droplets, such as in flight, where water droplets and/or ice may be entrained in air, and where measurements of total air temperature, relative humidity, pressure, mass flow rate, etc. are desired. Operating aircraft in icing conditions brings some risks. Conditions favourable to ice accretion can be critical for determining safe operating conditions of an aircraft. Equipping aircraft to safely operate in icing conditions may be expensive, and, given a want for accurate prediction of local airspace conditions, a safety margin for aircraft unequipped for flight in icing conditions, may lead to less effective utilization of the aircraft. Moreover aircraft equipped for such flight may need to detect icing conditions for safe operation. Currently no commercially available probes are known to reliably provide both total air temperature (herein TAT) and humidity, even though hygrometers exist, and TAT sensors are known using heated probes (where the heating is controlled to avoid contaminating the TAT measurement, and avoid icing).

The ice crystal and mixed phase icing environments are particularly problematic because substantial heat is required to avoid anti-icing, and this heat risks contaminating the TAT measurements and airborne liquid water content that can contaminate the humidity measurements.

A variety of sensor designs have been proposed. For example, U.S. Pat. No. 8,182,140 to Severson teaches a flow housing on an aircraft skin that has a hollow strut, and a foreaft facing flow tube mounted onto the strut. Free stream air flows through the flow tube and is controlled by an opening at the aft end. A branch flow channel is provided in the strut, and various sensor arrangements are shown.

A similar design is disclosed in U.S. Pat. No. 6,622,556 to May, housing a sample chamber for receiving a first flow diverted from the primary flow path, and an ancillary chamber adjacent to the sample chamber for receiving a second flow diverted from the primary flow path. May teaches a serpentine path through the sensor air flow paths and an aspirator for controlling air flow through the flow chamber.

U.S. Pat. No. 7,370,526 to Ice shows a similar skin-mounted sensor, showing expressly where a total air temperature TAT sensor, and a humidity sensor (inter alia), are to be located. In one embodiment, a flow controlled pressure source (e.g. a fan or pump) is used to control aspiration of a secondary chamber which houses a sensor.

As will be noted in relation to each of these teachings, one important characteristic of these sensors is the ability to preclude ingestion of water droplets and ice from the free stream air flow into the diverted air flows presented to the sensors. Presence of water or ice typically impairs the sensor. This is a considerable problem with the common design of each of these.

An equal problem is encountered in wind tunnels equipped for producing extreme mixed phase icing environments. Researchers have worked on solving the same problem in this context. A variety of embodiments have been tried in this context too. For example, a publication 2011-38-0036 of SAE International published Jun. 13, 2011, entitled *Naturally Aspirating Isokinetic Total Water Content Probe: Wind Tunnel Test Results and Design Modifications*, to Applicant's Craig Davison, Thomas Ratvasky of NASA, and Lyle Lilie of Science Engineering Associates, shows a design with three sensors in a wind tunnel. FIG. 22 specifically shows a Background Humidity Sampling Probe, an isokinetic IKP and a hot wire probe HWP. The Background Humidity Sampling Probe has a shape of a thickened pipe end, with a gradual thickening of the pipe wall towards the end, which faces downstream.

Orienting the probe inlet opposite to the flow does not accomplish the desired separation, at least in some flow regimes (see p. 4):

"In some cases the measured humidity level by the LiCor implied greater than 100% relative humidity at the spray bars. This was assumed to be caused by the relatively warm water and air injected through the spray nozzles providing the energy to evaporate more water than would be possible if everything was at ambient conditions. This occurred more often at lower velocities and higher LWC levels which would maximize the energy available and minimize the cooling effect, maximizing the available energy from the water for evaporation. Fortunately, as this phenomenon occurred more often at higher LWC levels the effect on the final TWO result was usually small so if the assumptions presented are incorrect the error was minimal."

An aspect not mentioned here is that, high liquid water content (LWC) and low velocity (i.e. where the worst contamination was observed) represents the worst condition for entrainment of droplets. At low velocity, due to lower momentum of the droplets, they are more easily drawn in by the sample airflow and the low drag that would remove droplets from the inlet edge of the probe. These probe inadequacies would provide the results that were observed where the humidity was overestimated, i.e. >100%.

More directly, an excerpt from p. 5 states:

"In some cases the background humidity probe appears to have ingested a large quantity of liquid water. An example is shown near the 70 second point in FIG. 5. The LiCor reading increases rapidly and the TDL and Vaisala TWO readings show a corresponding drop. The raw TDL reading, however, shows no corresponding change. If it was truly an increase in background humidity we would expect to see an increase in the raw TDL reading and a resulting constant value for the TDL TWO. It is not until 220 seconds, 150 s after the initial ingestion, that the liquid water in the LiCor tubing appears to have fully cleared."

A solution is needed to improve the separation of droplets and ice entrained in a free stream air flow, or like particulate laden gas stream, and provides a particulate free flow for sampling the free stream air flow.

SUMMARY OF THE INVENTION

Applicant has discovered that substantial improvement over the design of publication 2011-38-0036 can be made by careful attention to an opening of the downstream facing probe inlet. Working on the assumption that water from the flow may bead along the downstream face of the thick end, and accumulate on the thickened annular wall at the opening of the probe, where the flow is well shielded, Applicant designed a probe with a flared end, having a similar outer profile to that of the NASA probe, but having a thin rim, and found an unexpected improvement. Entrainment has not been a problem in testing in a mixed phase flow over a wide range of conditions.

Applicant hereby incorporates by reference an exact copy of the claims as recited below.

Accordingly, an air sensor for sampling air in a stream is provided, the sensor comprising a body defining an enclosed channel, the channel defining a unidirectional flow path for sampled air between an ingress and an egress; the ingress having an opening to the stream, facing downstream, and no opening to the ingress facing upstream; the egress providing a flow through the enclosed channel; a device for measuring a property of sampled air retained within the channel; and a feature for mounting the body in a fixed position with respect to the stream, wherein the opening has a peripheral edge with an average thickness of 5 mm or less.

The opening may be defined by a wall having a stream-adjacent face, an internal face opposite the stream-adjacent face, and the edge defined between the two faces. The stream-adjacent face may surround the ingress. A cross-sectional area of the stream-adjacent face may increase monotonically in a direction of the stream, and is greatest near the edge to encourage shedding.

The body may be tubular. The opening may be at an open flared end of the tubular body, to provide enlargement of the cross-sectional area occupied by the air sensor, in a direction of the stream. The tubular body may be substantially straight, and extend substantially parallel to the direction of the stream, or may have a single bend connecting a first segment and a second segment, the first segment coupling the air sensor to a body adjacent to the stream, and the second segment extending substantially parallel to the stream.

The ingress may be defined only by a flared open end of the tubular body; or the ingress may be defined between an open end of a bonnet and at least a tip of an outer wall of the tubular body, the bonnet having a greater radial extent than the tubular body.

The flaring may have a 1-170° included angle, more preferably a 65°-85° included angle.

The air sensor may be mounted to an aircraft, for example at a position that is protected from supercooled liquid water icing; to an airfoil; or to a vertically extended stabilizer.

The egress may be coupled to a static low pressure source that is defined by the action of the stream on an aircraft to which the air sensor is mounted. The egress may further comprise a flow control device for varying a flow rate through the channel. The egress may further comprise a mass flow sensor for regulating the flow control device.

The body may be a monocoque housing. The average thickness may be less than 2.5 mm. The sensor may measure one or more of: temperature, humidity, air pressure, and mass flow rate.

Also accordingly, a method for measuring a property of air in a stream is provided. The method comprises: providing an opening to the stream for a sensor, the opening facing downstream, and providing no opening to the stream facing upstream, the opening having a peripheral edge thin enough to limit beading around the opening; placing a sensor for measuring the property in fluid communication with the opening; and drawing sampled air from the stream through the opening and across the sensor, and ejecting the sampled air from the sensor so that only newly sampled air passes across the sensor.

The peripheral edge of the opening may be flared to increase a cross-section of an outer face of the opening that is adjacent the stream near the opening, to improve shedding around the opening.

The peripheral edge may have an average thickness less than 2.5 mm. The opening may be defined only by a flared open end of a tubular body for housing the sensor. The opening may be defined between an open end of a bonnet and at least a tip of an outer wall of a tubular body for housing the sensor, the bonnet having a greater radial extent than the tubular body. The tubular body may be substantially straight, and extend substantially parallel to the direction of the stream. The tubular body may have a single bend connecting a first segment and a second segment, the first segment coupling the air sensor to a body adjacent to the stream, and the second segment extending substantially parallel to the stream. The sensor may be adapted to sense one or more of: temperature, humidity, air pressure, mass flow rate, and particle density.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIG. 11 is a plot showing typical data extracted from the altitude chamber, showing measured dewpoint and total air temperature, as well as water supply rates.

DESCRIPTION OF PREFERRED EMBODIMENTS

Herein an air sensor is described, having improved separation of entrained particles from a stream of air, into the sensor. Herein 'particle' is to be understood to mean solid or liquid material having dimensions in a range from about 3 cm to 300 nm, but typically refers to atmospheric water droplets and ice, and pollution. The sensor is preferably mounted on an aircraft, or other structure that is subject to such a stream.

Figure 1:
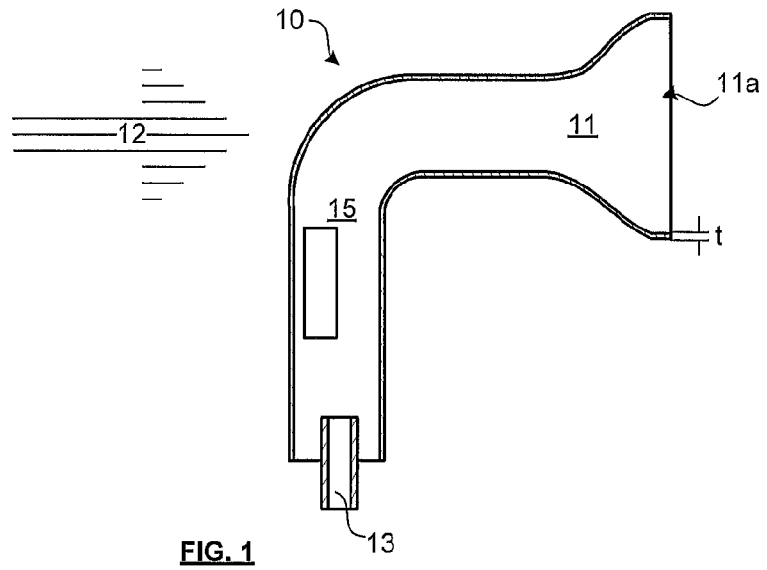
FIG. 1 is a schematic illustration of a bent tube air sensor in accordance with an embodiment of the present invention.

FIG. 1 is a schematic illustration of a first embodiment of a sensor 10 in accordance with the invention. The sensor 10 includes a housing having; an entry channel 11 with an opening 11a oriented to face substantially downstream of a stream of air (direction identified by arrow 12), an instrumented flow path 15 in fluid communication with the entry channel 11, and an egress 13 for removing air after flow through the instrumented path 15.

An edge of the opening 11a is chosen to have a thickness, t, ranging from a knife edge up to about 5 mm, more preferably t is less than 2.5 mm, and most preferably t is less than 1 mm: the purpose being to prevent particulates accreting, such as liquid water pooling, on the downstream facing surface.

A flaring of the opening 11a is chosen to direct shedding of the stream away from the inlet. Aerodynamic drag on the outer surface of the flare promotes shedding and minimizes ingestion of particulates in the stream. In accordance with the present invention, the flaring may be 1°-170° included angle but preferably is from 65°-85°. While the flaring is shown as a double curve with a first curve transitioning from a cylindrical wall to a conic wall, and a second curve transitioning from the conic wall to a cylindrical wall of greater diameter, it can equally be a straight conic flare, or may have an additional outward curve at its lip. It should be noted that the flaring need not have radial symmetry. For example, entrainment rates will vary with angle if the shape is not radially symmetric, and this may be useful if the flow varies azimuthally. Alternatively, active elements, such as a dielectric barrier discharge DBD device (or other cold-plasma) may be used to accelerate the stream away from the opening 11a. Coatings on the outer surface of the entry channel 11 near opening 11a, such as super-hydrophobic coatings, can be used to promote the shedding of surface liquids, especially if the current limitations on the longevity of these coatings are improved.

Conveniently, the housing of sensor 10 is shown with a monocoque structure that serves to support the sensor, for example by mounting an end to an outer surface of the aircraft, while housing the instrumented path 15, and providing a unidirectional flow with removal via the egress 13 that reduces thermal contamination by ensuring no backflow of imbibed air. The housing illustrated is a bent tube with a flared end. Typically a robust housing and mounting is desired, to suffer impact with the occasional bird, or severe winds and hail, and to be aerodynamically optimized for the specific installation. There is nothing essential about this housing but that it be suitable for the application, have an opening 11a facing downstream, have a thin edge around the opening to minimize pooling of particulates, and to not interact with the stream in a way that encourages entrainment, for example by the flaring, or other suitable mechanism. If the housing is near a heat source, it is preferably insulated. It is preferably mounted away from icing surfaces, which are generally the forward facing surfaces of the aircraft.

While each illustrated embodiment shows the entry channel 11 with a circular outer edge, it will be appreciated that this is not strictly necessary. Circular openings 11a are preferred because of the higher surface area to periphery ratio and simplicity of manufacture, but an oval or flattened circular (rounded rectangular) opening may be used. Alternatively, a 3 dimensional opening having a scooped profile, for example, that compensates for an asymmetry of the flow resulting from a geometry of a mounting of the sensor, the sensor, and an airfoil to which it is mounted, may be used.

It is generally preferable to ensure a draw through egress 13 is sufficient to maintain satisfactory sampling of the stream for a range of operating conditions. This may be provided by coupling egress 13 to a suitably low pressure source, which may be a fixed, provisioned, low pressure source that derives from the operation of the aircraft, or by a mechanical flow control element, such as a pump or blower, or a variable size opening to the low pressure source, for example.

For aeronautics applications in a mixed phase air flow, the inlet velocity may be maintained below 30 m/s with the ideal range being 2 to 10 m/s, to avoid the entrainment of water and ice, and to minimize compressibility effects which will affect the temperature measurement accuracy.

Figure 2:
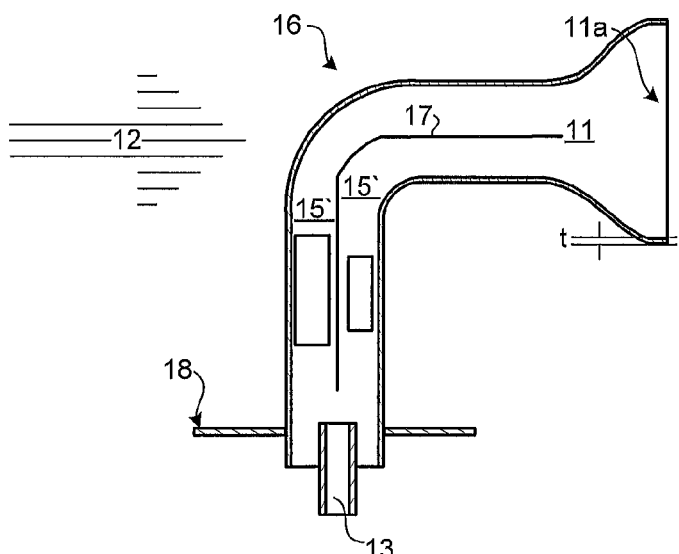
FIG. 2 is a schematic illustration of a dual compartment bent tube air sensor in accordance with an embodiment of the present invention.

Applicant prefers placing an air temperature sensor approximately 1.5 times an inner diameter of the sensor downstream of the inlet chamber opening. Generally there is a trade-off between thermal equilibrium FIG. 2 is a schematic illustration of a second embodiment of a sensor 16 in accordance with the invention. Herein features of like reference numerals in different figures are corresponding features and their descriptions are not repeated. The second embodiment differs from the first in that two instrumented paths 15' are provided by the insertion of a separating wall 17 within the instrumented path 15 of the first embodiment, although it will be appreciated that other manifolds may be provided to divide the stream through the entry channel 11 in various ways, as may be desirable for respective applications. For example, despite a turbulent flow, one instrumented path 15 may be less prone to particle entrainment, and may house sensors more sensitive to entrainment. Alternatively, sensors that affect the flow, may not contaminate or affect subsequent sensors if the streams are divided. The separating wall 17 may be thermally insulated to reduce heat transfer between the instrumented paths 15', and may extend through the housing to further reduce thermal coupling. Furthermore, while the separating wall 17 extends through the sensor 16 within the instrumented path 15, allowing for the streams to rejoin for a given length before the egress 13. In alternative embodiments each instrumented path 15' is coupled to a respective egress.

The embodiment of FIG. 2 further shows meeting of the sensor 16 to an outer surface 18 of an aircraft. As such, a mean depth of the opening 11a may lie in a boundary flow for a certain range of operating conditions, which is an important parameter for design of the sensor 16, with which a velocity of the local flow and pressure at the opening 11a depend. The sensor 16 may be telescopically mounted to adjust the depth to correspond with desired operating conditions, or for different sensor modalities.

One feature of the bent tube design shown in FIGS. 1,2 is that the body of the tube, especially near the bend and prior to the bend, present a buff body that shields the opening against the stream.

Figure 3:
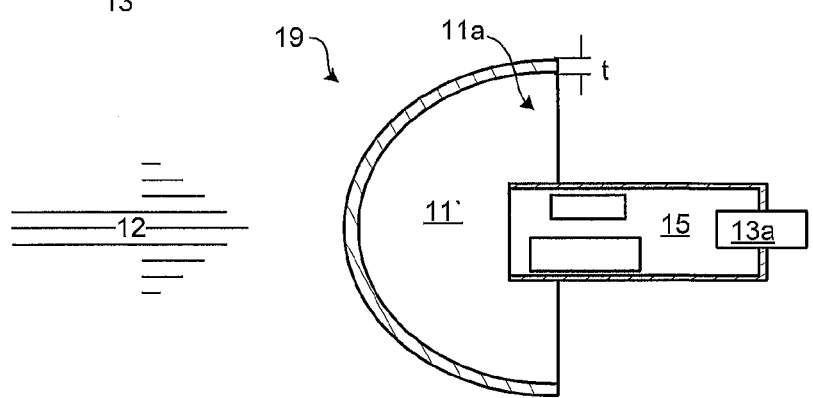
FIG. 3 is a schematic illustration of a two-part air sensor in accordance with an embodiment of the present invention.

FIG. 3 is a schematic illustration of a third embodiment of a sensor 19, in accordance with the present invention. Sensor 19 has a two-part housing including a bonnet 11', and the instrumented path 15 housing. The bonnet 11' generally houses the entry channel, and has its opening 11a facing downstream. The entry channel provided between the bonnet 11' and an outer wall of the instrumented path 15 housing is somewhat torturous compared with the entry channel 11 of FIGS. 1,2. The opening 11a in the third embodiment has an annular shape, whereas the opening 11a of FIGS. 1,2 are circular. A distance the instrumented path 15 housing extends into the bonnet 11' defines an overlap distance, which may be negative, if the bonnet 11' is wide enough to satisfactorily exclude particles, but is preferably flush (i.e. no overlap) to an emersion distance where the clearance between 11' and the inlet, 11a, has a cross-sectional flow area at least ½ the minimum inner probe flow area of the flow path 15. Some overlap may be preferred to reduce entrainment at the expense of a longer path from the flow to the sensor. The bonnet 11' can be connected to the flow path 15 by a prismatic joint, for telescopic operation that allows for variation of the overlap, either for test and configuration purposes, or during operation, to improve control.

A flow cross-sectional area within the bonnet 11' that is greater than that of the instrumented flow path 15 may be advantageous for slowing down the air imbibed by the sensor 19, as larger cross-sectional areas result in lower velocities, which suspend fewer particles. To this end, a leading edge of the instrumented flow path 15 need not be a cylindrical wall, as shown, and may have a chamfer. The outer wall of the instrumented flow path 15 may be chamfered, and the inner wall may be chamfered outwardly to gradually decrease a flow cross-section for the flow transiting between the bonnet 11' Accordingly one or more particle traps may be provided on an inner wall of the bonnet 11'.

The sensor 19 may be mounted as two separate parts (bonnet 11' and instrumented path 15 housing), although preferably the two are mechanically connected e.g. by webs of reinforcing material (not illustrated), or by the prismatic joint, to ensure that relative movement is within acceptable limits.

The third embodiment includes an active flow control element 13a at the egress, which may be a mechanical pump such as a positive displacement or inertial air pump. The flow control element 13a may additionally have sensors for controlling a volume flow rate out of the instrumented path 15, with a view to limiting a variability of entrainment rates under changing operating conditions. In an alternative embodiment, a pressure sensor is mounted near the opening 11, and communicates with the flow control element 13a, to improve control over a volume flow rate through the flow path 15, under changing conditions. If the flow control element 13a has a variable flow rate, it may be controlled by a predictive algorithm and/or a feedback control loop, in a manner known in the art.

It will be noted that by adding a suitable bonnet 11' to a prior art sensor, as described in the background of the invention, it is believed that substantial improvements can be obtained in limiting the entrainment of particles, although doing so will complicate a device that is already more complicated than the present embodiments.

Figure 4:
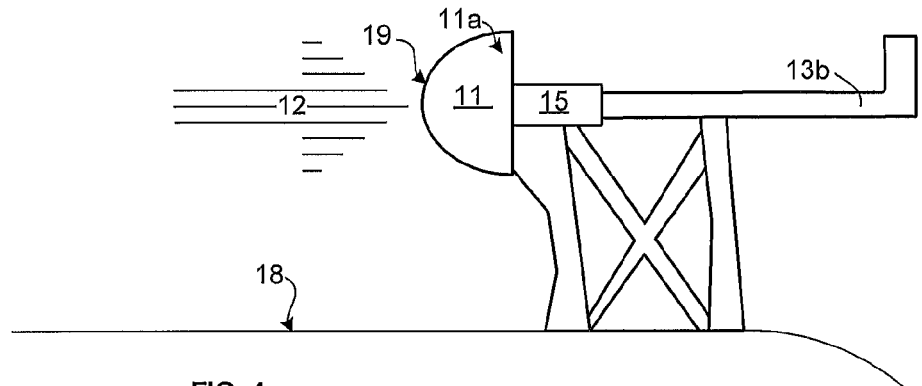
FIG. 4 is a schematic illustration of the two-part air sensor of FIG. 3 mounted on a surface of an aircraft.

FIG. 4 is a schematic illustration of a mounting of the sensor 19, with one modification. Instead of a flow control element 13a, an exhaust vent 13b is provided. The exhaust vent is open to a space where the pressure is lower relative to the inlet, in this case, beyond a trailing edge of the airfoil. Other examples of static pressure differences on, and around, aircraft include a high velocity airflow region or between the pressure and suction surfaces of a lifting airfoil.

A flow control element may be included in the exhaust vent 13b in the form of a controllable aperture for varying an effective diameter of the egress 13b, in order to control volume flow rate through the sensor 19. Alternatively, the vent 13b itself may be telescopic such that a depth into the flow can be varied to increase or decrease mass flow rate through the sensor 19.

Figure 5:
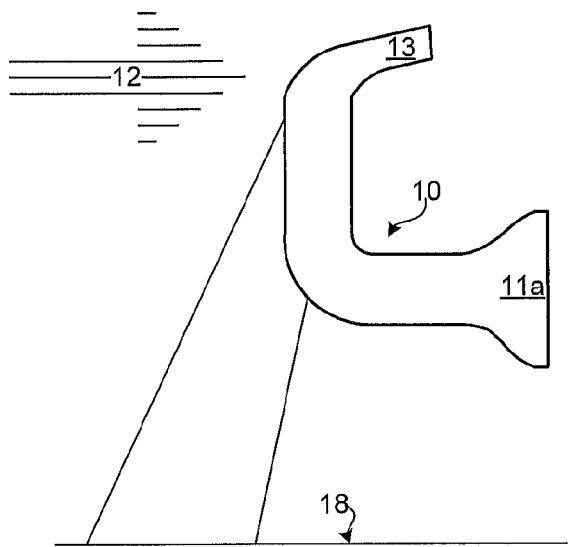
FIG. 5 is a schematic illustration of a bent tube air sensor of FIG. 1 with a distal discharge mounted on a surface of an aircraft.

FIG. 5 is a schematic illustration of another embodiment of the present invention. FIG. 5 shows a sensor 10, modified in the shape of the egress 13, and oriented so that the egress is further from the airfoil than the entry 11a. By the same principle, the boundary layer gradations will provide a natural pressure difference between 11a and 13.

Figure 6:
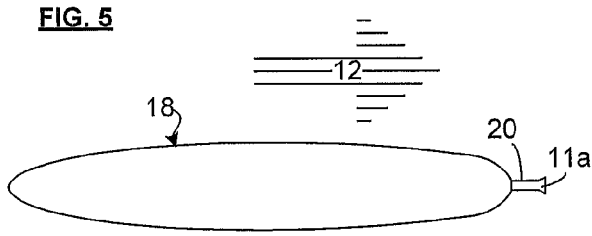
FIG. 6 is a schematic illustration of a straight tube air sensor of FIG. 1 mounted on a trailing surface of an airfoil.

The foregoing embodiments show mounting above a wing. FIG. 6 shows an embodiment where a sensor 20 is mounted at a trailing edge of an airfoil 18. The sensor 20 is shown disproportionately large, in order for it to be visible on the image. The Sensor 20 is essentially a straightened version of the bent tube embodiment of FIG. 1. An advantage of this embodiment is the minimization of drag introduced by the sensor 20.

Figure 7:
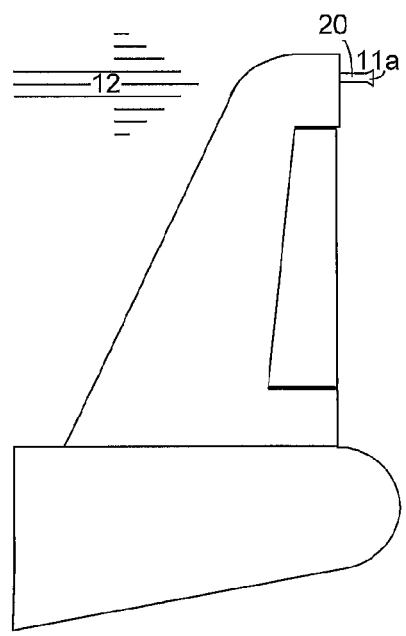
FIG. 7 is a schematic illustration of a straight tube air sensor of FIG. 1 mounted on a vertical stabilizer of a fixed-wing aircraft.

FIG. 7 is a schematic illustration of another embodiment of the invention, wherein sensor 20 is mounted to a vertical stabilizer of an airplane, above a rudder. The embodiments of FIGS. 6,7 show sensors that extend substantially parallel to a longitudinal axis of a fixed-wing aircraft.

In operation, air is extracted from the stream through the entry channel, and is drawn over one or more air measurement devices (e.g. for measuring temperature, humidity (or other air component concentration), pressure, air flow rate, density). The flare and orientation reduce particle (e.g. water, ice) ingestion, and the thinness of the trailing edge of the sensor is considered important for further reducing ingestion.

It will be appreciated by those of ordinary skill, that there may be advantages to mounting the sensor for controlled movement. For example, the flared opening 11a may be designed to swing over a limited arc, freely or with some elastic constraint, so that the opening faces directly downstream in the event of cross-winds. Another example is a telescopic joint that allows for the sensor to move in a direction (at least generally) normal to the surface to change a depth into the boundary layer from which the air is sampled. As the pressure as a function of normal distance from the surface is not linear, this can allow for a variation in mass flow rate through the sensor, as well.

Figures 8A, 8B, 8C, 8D, 8E:
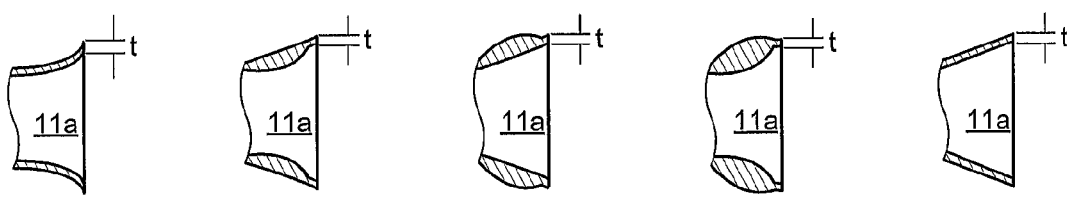
FIGS. 8a-e are cross-sections of exemplary downstream-facing openings for the air sensors, in accordance with examples of the present invention.

FIGS. 8a-e are schematic illustrations of openings 11a in accordance with various embodiments of the invention. FIG. 8a shows a uniform thickness, or gradually thinned single curvature flared end wall. FIGS. 8b-c show thickened end walls that narrow at the end face, respectively having a straight outer wall and a curved inner wall, a straight outer wall and a curved inner wall, and curved inner and outer walls. FIG. 8e shows a straight conical flaring end wall. Each of these could have an opening that is not planar, for example to define a scooped shape, for example, and could further have some protection against entrainment of larger size object, in the form of a wire mesh cover, for example. Preferably this would be bonded to an interior surface below the end wall identified as having the thickness t, to reduce surface flow of liquids from the outer wall to the wire mesh cover. As mentioned above, the cross-sectional shape of the opening 11a may be circular, elliptical, polygonal, or a polygonal with curved edges, but preferably has a reasonably high ratio of surface area to periphery.

Experiment

The design of a sensor was tested in an icing, high altitude, wind tunnel. The wind tunnel has an altitude chamber having one end coupled to a compressor, and a second end open to a supply of chilled air, and a supply of water droplets, and ice particles. The test chamber has a side wall through which the sensor of FIG. 1 extends. This facility reproduces conditions seen by aircraft in flight in mixed phase, glaciated and super cooled liquid water icing conditions.

Figure 9:
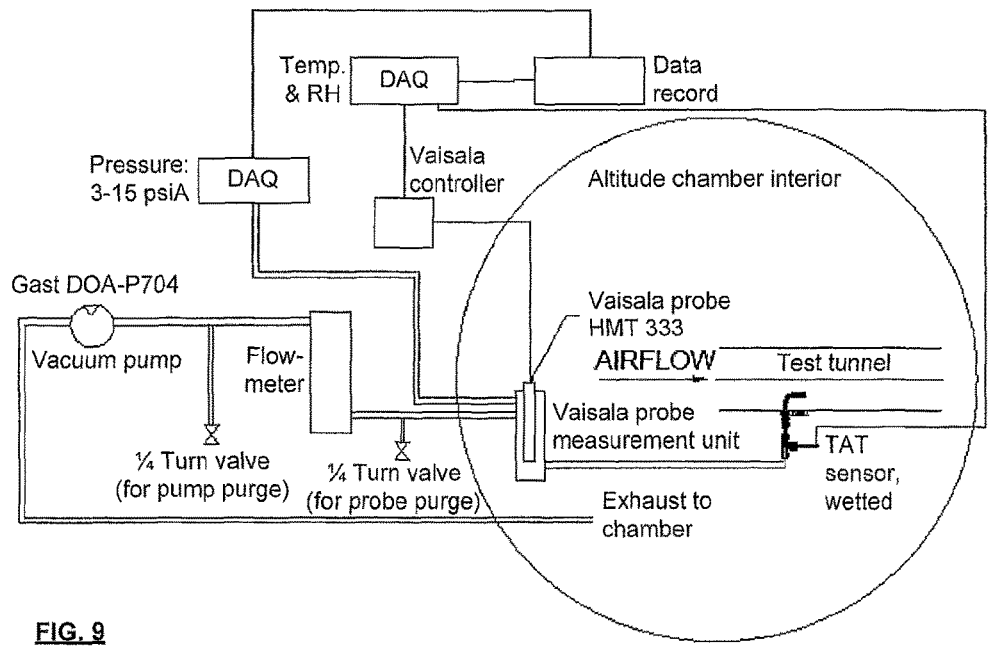
FIG. 9 is a schematic of an altitude chamber used for testing the present invention.
Figure 10:
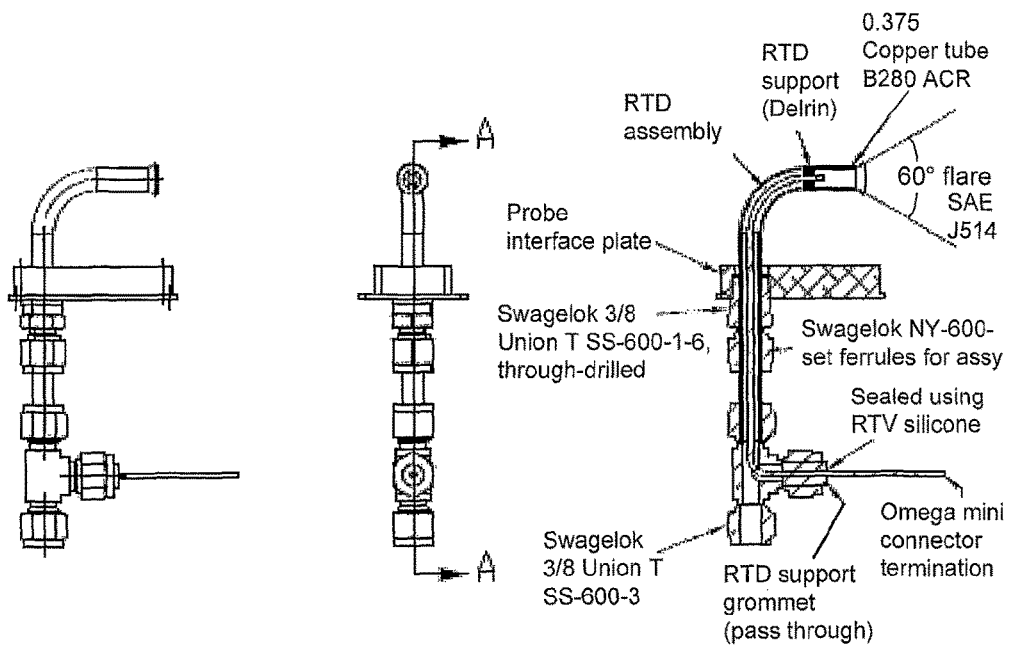
FIG. 10 schematically illustrates side and rear views of a probe used for the tests.

FIG. 9 is a schematic illustration of the tunnel design chosen for testing, and a sensor arrangement. A bent tube opening, as shown in FIG. 10, is inserted into a stream of a test tunnel with its opening facing downstream. The bent tube opening supplies air extracted from the stream to a TAT sensor, that is wetted. The TAT sensor measures temperatures and these are communicated electronically to a first Data AcQuisition board (DAQ). Specifically the TAT sensor is a resistance temperature device (RTD). Air drawn past the TAT sensor is coupled to a Vaisala probe measurement unit, via flexible tubing to permit telescopic movement of the bent tube opening, to permit sampling at different depths into the test tunnel.

The Vaisala probe measurement unit includes a HMT 333 probe in a controlled manifold. The probe is coupled electronically to a Vaisala controller, which is coupled to the first DAQ board. A flexible tube connects the manifold of the Vaisala probe measurement unit to a pressure transducer of a second DAQ, to record a pressure in the manifold. The DAQ boards are conventional measurement interfaces to a general purpose computer, which performs some operations on the data and records the measurements in a manner well known in the art. A panel mount visual flowmeter (vertically mounted) is provided downstream of the temperature and humidity measurement equipment. A vacuum pump (Gast DOA-P704) is provided downstream of the flow-meter. Two valves are provided between the vacuum pump and flowmeter, and between the flowmeter and Vaisala probe measurement unit to permit purging. The vacuum pump exhausts to the chamber. Of these instruments, only the Vaisala probe and temperature measurement units are located within the altitude chamber.

The pressure and temperature are measured at the Vaisala probe measurement unit in order to calculate the absolute moisture content, such as the mixing ratio, i.e. the mass of water versus the mass of dry air. A Vaisala controller (which acts as a signal conditioner for the Vaisala probe) is mounted and connected to the end of the probe, outside of the duct. Humidity can be measured with a number of different devices but specifically for this test, a Vaisala DMT330 was provided, and a pressure transducer designed for operation in a flow of 3-15 psia, was used at the second DAQ.

The tubing that interconnects the instruments are generally copper tubing, with some flexible tubing, as required. The inner diameter of the tubing matches that of the bent tube opening.

The air is extracted using a vacuum pump which has its outlet also in the altitude environment to minimize flow changes due to altitude changes. The airflow rate drawn through the probe is about 5 to 25 standard liters/minute. This value is important as: too fast a draw will entrain particles and/or droplets; and too slow a draw will both cause a slow response time and could allow heat to transfer with the inner probe walls.

The bent tube opening is illustrated in FIG. 10. A flared end of the probe has a 60° flare (SAE J514). The bent tube opening is made of copper (although a later embodiment used stainless steel, which works just as well), and is secured to a probe interface plate at the periphery of the test tunnel, for prismatic movement. Temperature can be measured with a number of different devices, including using a resistance thermal device (RTD), which was chosen for its accuracy and response time. The RTD sensor is supported near an entrance of the bent tube opening, specifically in the middle of the duct about 1.5 internal diameters away from the entrance. This location is important. To avoid any influence from particles or droplets that are light enough to be caught in vortices near the entrance, or imperfectly shed along the rim, it is desired to set the RTD far enough behind the entrance. At the same time, excessive set back risks that heat exchange with the tube wall influence a measured temperature. The RTD has a wired coupling that passes through the tubing in a sealed manner, to output to the first DAQ. The bent tube opening is coupled to a first section of horizontal tubing that couples to the Vaisala probe measurement unit, as shown in FIG. 9.

The humidity too can be measured by a number of types of sensor types but for our existing probe, the Vaisala probe uses a capacitance type sensor. This sensor has reasonable accuracy and importantly has a desired response time. This apparatus can reach a steady state response typically in 15 seconds or less, for both TAT and humidity measurements. This is important in wind tunnel testing, as a test point is generally short in duration (a few minutes) and therefore there is not a lot of time available for a probe to stabilize. On an aircraft, this constraint may be relaxed. This mixing ratio can then be used to determine the dewpoint or relative humidity under the measured tunnel conditions.

Another aspect of a downstream facing opening is that the pressure in the line is lower than the total in the tunnel. This decreases the relative humidity (RH), which reduces condensation that would significantly affect the accuracy of the RH measurement. As the RH in the test tunnel depends on the pressure drop between the sensors and the test tunnel, the pressure is measured in the Vaisala probe measurement unit to correct for this. In some embodiments it may be necessary to take steps to prevent condensation on the tubes between the opening and RH measurement device. As well, this aspect can be advantageous for high humidity operating regimes, because many hygrometers loose accuracy at high RH values and this reduction in RH can move the measurement to a more accurate regime for the sensor.

Applicant has tested this sensor in a variety of operating conditions, and has found no problems with the measurements. The measurements from the hygrometer confirm the results of this energy and moisture balance throughout the operating envelope tested.

Sample results from the RH/TAT sensor are presented in FIG. 11. The figure is a graph showing the variation of test section dew point, total air temperature and water flow rate to the spray mast, all as a function of with time. The instances where the water flow to the mast is turned on and off are marked by solid vertical lines. The test section operating pressure is held constant at 4.4 psia throughout the test. Prior to the water flow being turned on, the test section total air temperature was 23° C. and the dew point was −19.5° C. The low operating pressure and initially warm, dry air resulted in significant evaporation of the spray once the water flow to the tunnel commenced (i.e. water directed to nozzles). The rapid decrease of total temperature and increase of dew point is a result of this evaporation. The drop in air temperature is consistent with the energy required to evaporate the water spray as measured by the sensor.

The sensor reaches a steady state reading for both temperature and dew point roughly 20 seconds after the water spray is initiated. Once steady state is reached, there is negligible change in the sensor readings. This is further evidence that there is no entrainment of runback water or airborne droplets into the continuously extracted sample.

In general, it can be said that the sensor has a good response time and exhibits no liquid water entrainment for a severe test condition (high water flow, small droplet sizes, high altitude, and low Mach number).

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. An air sensor for sampling air in a stream, the air sensor comprising:
    a body defining an enclosed channel between an ingress and an egress;
    a mounting of the body to an aircraft in a fixed position with respect to the stream, the stream being produced by airflow around the aircraft during flight, the mounting orienting the ingress to present an opening thereof to the stream facing downstream, and presenting no opening to the ingress facing upstream;
    the egress ensuring a unidirectional flow path for sampled air through the enclosed channel from the ingress to the egress; and
    a device for measuring a property of sampled air flowing through the channel;
    wherein the opening is provided at a flared end of the body that provides an enlargement of a cross-sectional area occupied by the air sensor, and has a peripheral edge with an average thickness of 5 mm or less.

2. The air sensor of claim 1 wherein the opening is defined by a wall having a stream adjacent face, an internal face opposite the stream-adjacent face, and the edge defined between the two faces; and wherein the stream-adjacent face surrounds the ingress.

3. The air sensor of claim 2 wherein a cross-sectional area of the stream-adjacent face increases monotonically in a direction of the stream, and is greatest near the edge to encourage shedding.

4. The air sensor of claim 1 wherein the body is tubular.

5. The air sensor of claim 4 wherein the tubular body:
    is substantially straight, and extends substantially parallel to the direction of the stream; or
    has a single bend connecting a first segment and a second segment, the first segment coupling the air sensor to a body adjacent to the stream, and the second segment extending substantially parallel to the stream.

6. The air sensor of claim 4 wherein the ingress is defined only by a flared open end of the tubular body; or the ingress is defined between an open end of a bonnet and at least a tip of an outer wall of the tubular body, the bonnet having a greater radial extent than the tubular body.

7. The air sensor of claim 4 wherein the flaring has a 65°-85° included angle.

8. The air sensor of claim 1 mounted to the aircraft: at a position that is protected from supercooled liquid water icing; to an airfoil; or to a vertically extended stabilizer.

9. The air sensor of claim 1 wherein the egress is coupled to a static low pressure source that is defined by the action of the stream on an aircraft to which the air sensor is mounted.

10. The air sensor of claim 1 wherein the egress comprises a flow control device for varying a flow rate through the channel; and optionally further comprising a mass flow sensor for regulating the flow control device.

11. The air sensor of claim 1 wherein: the body is a monocoque housing; or the average thickness is less than 2.5 mm.

12. A method for measuring a property of air in a stream, the method comprising:
    providing a body mounted on the aircraft with an opening to the stream for a sensor, the opening facing downstream, and providing no opening to the stream facing upstream, the opening provided at a flared end of the body that provides an enlargement of a cross-sectional area occupied by the air sensor, and having a peripheral edge thin enough to limit beading around the opening;
    placing a sensor for measuring the property in fluid communication with the opening; and
    drawing sampled air from the stream through the opening and across the sensor, and ejecting the sampled air from the sensor so that only newly sampled air passes across the sensor.

13. The method of claim 12 wherein the peripheral edge of the opening is flared to increase a cross-section of an outer face of the opening that is adjacent the stream near the opening, to improve shedding around the opening.

14. The air sensor of claim 12 wherein providing the opening comprises providing an opening that is defined only by a flared open end of a tubular body for housing the sensor.

15. The air sensor of claim 12 wherein the peripheral edge has an average thickness less than 2.5 mm, or the sensor is adapted to sense one or more of: temperature, humidity, air pressure, mass flow rate, and particle density.

16. An air sensor for a fixed-wing aircraft, the air sensor extending outwardly from the aircraft from a rear-facing wall of the aircraft, substantially on or parallel to a longitudinal axis of the aircraft.

17. The method of claim 12 wherein providing the opening comprises providing an opening that is defined between an open end of a bonnet and at least a tip of an outer wall of a tubular body for housing the sensor, the bonnet having a greater radial extent than the tubular body.

18. The method of claim 12 wherein providing the opening comprises providing a tubular body that is substantially straight, and extends substantially parallel to the direction of the stream, for the sensor.

19. The method of claim 12 wherein placing the sensor comprises providing a tubular body for the sensor that has a single bend connecting a first segment and a second segment, the first segment coupling the air sensor to a body adjacent to the stream, and the second segment extending substantially parallel to the stream.

20. The air sensor of claim 1 wherein the sensor is adapted to sense one or more of: temperature, humidity, air pressure, mass flow rate, and particle density.

* * * * *